United States Patent
Lay et al.

(10) Patent No.: US 10,079,071 B1
(45) Date of Patent: *Sep. 18, 2018

(54) METHOD AND SYSTEM FOR WHOLE BODY BONE REMOVAL AND VASCULAR VISUALIZATION IN MEDICAL IMAGE DATA

(71) Applicant: Siemens Healthcare GmbH, Erlangen (DE)

(72) Inventors: Nathan Lay, Bethesda, MD (US); David Liu, Plano, TX (US); Shaohua Kevin Zhou, Plainsboro, NJ (US); Bernhard Geiger, Cranbury, NJ (US); Li Zhang, Terhune Road, NJ (US); Vincent Ordy, Plainsboro, NJ (US); Daguang Xu, Princeton, NJ (US); Chris Schwemmer, Forchheim (DE); Philipp Wolber, Singapore (SG); Noha Youssry El-Zehiry, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/021,881

(22) Filed: Jun. 28, 2018

Related U.S. Application Data

(63) Continuation of application No. 14/703,132, filed on May 4, 2015, now Pat. No. 10,037,603.

(51) Int. Cl.
*G06T 7/00* (2017.01)
*G16H 30/40* (2018.01)
(Continued)

(52) U.S. Cl.
CPC ............. *G16H 30/40* (2018.01); *G06T 5/005* (2013.01); *G06T 7/11* (2017.01); *G06T 19/00* (2013.01);
(Continued)

(58) Field of Classification Search
CPC ......... G06T 7/0081; G06T 7/11; G06T 5/005; G06T 19/00; G06T 2200/04;
(Continued)

(56) References Cited

U.S. PATENT DOCUMENTS 6,754,376 B1 * 6/2004 Turek .................... G06T 7/0012
382/131
7,676,257 B2 * 3/2010 Suryanarayanan .... A61B 6/481
382/128
(Continued)

*Primary Examiner* — Sean Motsinger

(57) ABSTRACT

A method and apparatus for whole body bone removal and vasculature visualization in medical image data, such as computed tomography angiography (CTA) scans, is disclosed. Bone structures are segmented in the a 3D medical image, resulting in a bone mask of the 3D medical image. Vessel structures are segmented in the 3D medical image, resulting in a vessel mask of the 3D medical image. The bone mask and the vessel mask are refined by fusing information from the bone mask and the vessel mask. Bone voxels are removed from the 3D medical image using the refined bone mask, in order to generate a visualization of the vessel structures in the 3D medical image.

23 Claims, 15 Drawing Sheets

(51) Int. Cl.
*G06T 7/11* (2017.01)
*G06T 19/00* (2011.01)
*G06T 5/00* (2006.01)

(52) U.S. Cl.
CPC ............... *G06T 2200/04* (2013.01); *G06T 2207/10081* (2013.01); *G06T 2207/30008* (2013.01); *G06T 2207/30101* (2013.01); *G06T 2210/41* (2013.01)

(58) Field of Classification Search
CPC . G06T 2207/10081; G06T 2207/30008; G06T 2207/30101; G06T 2210/41
See application file for complete search history.

(56) References Cited

U.S. PATENT DOCUMENTS

| | | | |
|---|---|---|---|
| 7,839,403 B2 * | 11/2010 | Heigl | G06T 15/08 345/423 |
| 8,068,655 B2 | 11/2011 | Odry et al. | |
| 8,244,015 B2 | 8/2012 | Sirohey et al. | |
| 8,837,771 B2 | 9/2014 | Lay et al. | |
| 2005/0113679 A1 * | 5/2005 | Suryanarayanan | A61B 6/481 600/425 |
| 2005/0260658 A1 * | 11/2005 | Paladini | G06K 9/346 435/6.19 |
| 2006/0122501 A1 * | 6/2006 | Lara-Montalvo | A61B 5/02007 600/425 |
| 2008/0118127 A1 | 5/2008 | Sirohey et al. | |
| 2009/0012382 A1 * | 1/2009 | Dutta | A61B 5/02007 600/407 |
| 2009/0087071 A1 * | 4/2009 | Chen | G06T 5/002 382/132 |
| 2009/0100105 A1 * | 4/2009 | Mutchler | G06Q 50/22 |
| 2009/0136106 A1 * | 5/2009 | Roberts | G06T 15/08 382/130 |
| 2009/0208082 A1 * | 8/2009 | Westerhoff | G06T 7/0012 382/131 |
| 2010/0055099 A1 * | 3/2010 | Filvaroff | C12Q 1/6809 424/133.1 |
| 2010/0080434 A1 | 4/2010 | Seifert et al. | |
| 2010/0128954 A1 * | 5/2010 | Ostrovsky-Berman | G06T 7/11 382/131 |
| 2010/0296718 A1 * | 11/2010 | Ostrovsky-Berman | G06T 7/62 382/133 |
| 2012/0121147 A1 * | 5/2012 | Huang | G06T 7/32 382/131 |
| 2014/0161334 A1 * | 6/2014 | Wang | G06K 9/00362 382/131 |
| 2014/0294269 A1 * | 10/2014 | Mohr | G06T 7/0091 382/131 |
| 2015/0161782 A1 * | 6/2015 | Mohr | G06T 7/136 382/128 |
| 2015/0228072 A1 * | 8/2015 | Merckx | G06T 5/005 382/131 |
| 2016/0093096 A1 * | 3/2016 | Ouji | G06K 9/4604 382/131 |
| 2016/0228084 A1 * | 8/2016 | Nempont | A61B 6/461 |
| 2016/0328855 A1 * | 11/2016 | Lay | G06T 7/0081 |
| 2017/0258430 A1 * | 9/2017 | Pfister | A61B 5/489 |

* cited by examiner

METHOD AND SYSTEM FOR WHOLE BODY BONE REMOVAL AND VASCULAR VISUALIZATION IN MEDICAL IMAGE DATA

This application is a continuation of U.S. patent application Ser. No. 14/703,132, filed May 4, 2015, the disclosure of which is herein incorporated by reference.

BACKGROUND OF THE INVENTION

The present invention relates to bone removal and vascular visualization in medical image data, and more particularly, to removal of bone voxels from 3D computed tomography angiography images in order to visualize vessels in the 3D computed tomography angiography images.

Computed Tomography Angiography (CTA) is a medical imaging technique that is often used to visualize the blood vessels in a patient's body. Computed tomography (CT) combines a series of X-ray images taken from different angles and uses computer processing to create cross-sectional images, or slices, of bones, blood vessels and soft tissues inside the body. The cross-sectional images, or slices, can be combined to generate 3D CT volumes. In CTA, a contrast agent is injected into the bloodstream of the patient prior to CT imaging in order to generate contrast enhanced CT images that visualize the patient's vessels.

In CTA images, there is an overlapping intensity between distribution bones and contrast enhanced vessels. That is bone and contrast enhance vessels appear with similar intensity in CTA images. Accordingly, bones can be a major obstacle in the visualization and analysis of vessel trees, aneurisms, and calcifications using CTA, and it is desirable to remove bone structures from CTA images in order to achieve a better visualization of the vessels. In the past, manual editing techniques have been used to extract and remove bone structures from the image data. However, the tedious and long operating time required for manual editing is prohibitive for it to be of practical use. Furthermore, due to image resolution and noise in the image data, bones and vessels with overlapping intensity distributions often appear to be connected, which creates significant challenges in automated segmentation and removal of bone structures from the image data.

BRIEF SUMMARY OF THE INVENTION

The present invention provides a method and system for whole body bone removal and vasculature visualization in medical image data. Embodiments of the present invention perform independent segmentation for both bones and vessels in medical image data, such as computed tomography angiography (CTA) images, of a patient, and then fuse the independently performed bone and vessel segmentations. Embodiments of the present invention provide automated methods for bone segmentation and vessel segmentation in medical image data. Embodiments of the present invention also provide a system and method for editing medical image data in which bone removal has been performed.

In one embodiment of the present invention, bone structures are segmented in a 3D medical image, resulting in a bone mask of the 3D medical image. Vessel structures are segmented in the 3D medical image, resulting in a vessel mask of the 3D medical image, wherein segmenting bone structures in the 3D medical image and segmenting vessel structures in the 3D medical image are performed independently with respect to each other. The bone mask and the vessel mask are refined by fusing information from the bone mask and the vessel mask. Bone voxels are removed from the 3D medical image using the refined bone mask to generate a visualization of the vessel structures in the 3D medical image.

In another embodiment of the present invention, a multi-label atlas is registered to a 3D medical image. Bone and vessel structures are segmented in the 3D medical image using anatomy and location-specific segmentation based on the registered multi-label atlas. The bone structures are removed from the 3D medical image to generate a visualization of the vessel structures in the 3D medical image.

These and other advantages of the invention will be apparent to those of ordinary skill in the art by reference to the following detailed description and the accompanying drawings.

DETAILED DESCRIPTION

The present invention relates to a method and system for whole body bone removal and vasculature visualization in medical image data of a patient. Embodiments of the present invention are described herein to give a visual understanding of the bone removal and vasculature visualization method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
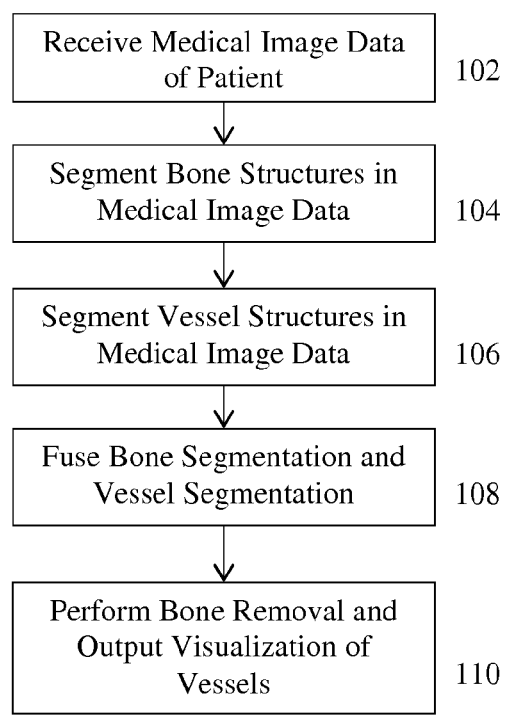
FIG. 1 illustrates a method for whole body bone removal and vasculature visualization in medical image data according to an embodiment of the present invention.

FIG. 1 illustrates a method for whole body bone removal and vasculature visualization in medical image data according to an embodiment of the present invention. The method of FIG. 1 transforms medical image data representing the anatomy of a patient to remove bone structures from the medical image data and generate a new medical image of the patient in which the bone structures have been removed and the vessel structures are enhanced. Although the method of FIG. 1 is described herein as being applied to computed tomography angiography (CTA) images of a patient, the present invention is not limited thereto and the method of FIG. 1 can be utilized with other types of medical image data as well.

At step 102, medical image data of a patient is received. The medical image data can be 3D medical image data of the patient acquired using computed tomography (CT), combined positron emission tomography (PET)-CT, or other imaging modalities, such as magnetic resonance imaging (MRI), ultrasound, etc. In an advantageous embodiment, the medical image data is a 3D coronary tomography angiography (CTA) image (i.e., contrast enhanced CT image), but the present invention is not limited thereto. In an advantageous embodiment, the medical image data is acquired using a whole body scan of the patient, however the method of FIG. 1 can be similarly applied to smaller regions of the patient as well. In an exemplary embodiment, the medical image data may a full body 3D CTA image of the patient. The medical image data of the patient can be received directly from an image acquisitions device, such as a CT scanner, or the medical image data of the patient can be received by loading medical image data previously stored on a memory or storage of a computer system or receiving the medical image data via a network transmission from another computer system.

At step 104, bone structures are segmented in the medical image data of the patient. The bone segmentation in step 104 is performed independently of the vessel segmentation in step 106, and results in a bone mask for the medical image data. Bone segmentation in CTA scans is challenging due to the varying appearance of vessels and bones and the proximity of vessels to bones. For example, the aorta is near vertebrae and the subclavian artery is near the clavicle and ribs. Bone itself varies in appearance being bright in the cortical bone and dark in the marrow. The cortical bone itself can be thin and can vary in intensity. For example, ribs sometimes have lower intensity while femurs have high intensity. It is important that vessels are not segmented as bone, as this may give the appearance of a stenosis or clot in the vessels once the bone structures are removed.

Figure 2:
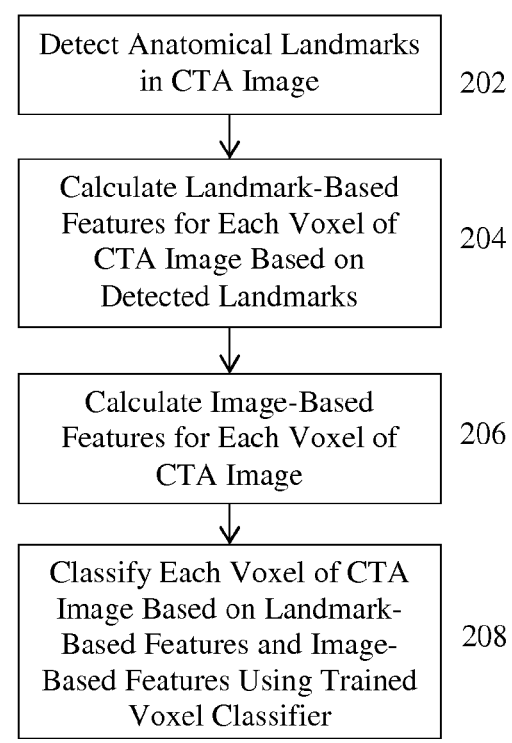
FIG. 2 illustrates a method for segmenting bones in computed tomography angiography (CTA) image data according to an embodiment of the present invention.

FIG. 2 illustrates a method of segmenting bones structures in a 3D CTA image of a patient according to an embodiment of the present invention. The method of FIG. 2 can be used to perform bone structure segmentation in step 104 of FIG. 1. The method of FIG. 2 performs machine learning-based bone segmentation that leverages anatomical knowledge to focus on only parts of the body with bones while rejecting parts of the body that lack bones. The method of FIG. 2 utilizes a trained voxel classifier, such as a trained Random Forest voxel classifier, that evaluates voxels in the medical image data using a combination of image-based and landmark-based features. In CTA scans, image appearance-based features, such as Haar features or Relative Shift Intensity Difference (RSID) features, tend not to discriminate well between vessel and cortical bone. However, Haar and RSID features can discriminate well between tissue and bone and marrow. Accord to an advantageous embodiment, to complement these image appearance-based features, the method of FIG. 2 utilizes landmark-based features that are calculated based on landmarks detected in the CTA image. These landmark features effectively reject regions of the CTA image that lack bone while focusing on regions in the CTA image with bone, while the image-based features discriminate between bone and tissue in the regions of the CTA image with bone.

Referring to FIG. 2, at step 202, a plurality of anatomical landmarks are detected in the CTA image. The plurality of anatomical landmarks can include anatomical landmarks throughout the body of the patient as well as organ centers for a plurality of organs of the patient. For example, the plurality of anatomical landmarks can include landmarks such as, but nor limited to, left and right lung tips, left and right humerus heads, bronchial bifurcation, left and right shoulder blade tips, inner left and right clavicle tips, sternum tip bottom, aortic arch, left and right endpoints of rib 11, bottom front and back of L5 vertebra, coccyx, pubica symphysis top, left and right corners of the hip bone, and organ centers of the heart liver, both kidneys, spleen, bladder, and prostate. A respective landmark detector can be trained for each landmark. In an advantageous embodiment, the trained landmark detector can be a Structured Regression Machine which provides fast landmark detection.

In one possible implementation, the landmark detection can be performed using trained landmark detectors connected in a discriminative anatomical network (DAN), as described in U.S. Patent Publication No. 2010/0080434, which is incorporated herein by reference in its entirety. In this implementation, predetermined key slices of the CTA image are detected and used to constrain a search space for each of the plurality of landmarks. Individual landmark detectors trained for each of the landmarks are then used to search the respective search space for each of the landmarks. The individual landmarks are connected in a DAN and the final landmark detection result for each of the landmarks is determined based on a probability response of the individual landmark detector combined with a probability from the DAN.

In another possible implementation, the landmark detection can be performed based on a series of structured regressions, as described in U.S. Pat. No. 8,837,771, which is incorporated herein by reference in its entirety. In this implementation, a nearest neighbor approach is used to calculate a respective displacement vector from a given voxel in the CTA image for each of the plurality of landmarks, resulting in a predicted location for each of the plurality of landmarks. This is performed for a number of voxels in the CTA image to generate a number of predictions for each landmark location, which define a local search region for each landmark. Individual trained landmark detectors for each landmark are used to evaluate the local search region for each landmark to detect the final detection result for each landmark.

At step 204, landmark-based features are calculated for each voxel of the CTA image based on the detected landmarks in the CTA image. In an advantageous implementation, the landmark-based features for a particular voxel in the CTA image include the L1 and L2 distances between that voxel and each of the landmarks and axial projections of the offsets between that voxel and each of the landmarks. The offset between a particular voxel V having coordinates ($x_V$, $y_V$, $z_V$) and a landmark L having coordinates ($x_L$, $y_L$, $z_L$) in the 3D CTA image can be expressed as a 3D vector ($\Delta x$, $\Delta y$, $\Delta z$) of the difference between the coordinate values for the voxel and the landmark. An axial projection of the offset is a 2D vector that projects the offset to a particular axial plane. For example, the axial projection ($\Delta x$, $\Delta y$) for an offset between a voxel and landmark projects that offset to the X-Y plane. According to a possible implementation, the axial projections of the offset to the X-Y plane, the X-Z plane, and the Y-Z plane can each be used as landmark-based features. These landmark-based features can be calculated for each of the voxels in the CTA image based on each of the detected landmarks.

At step 206, image-based features can be calculated for each voxel of the CTA image. For example, for each voxel or in CTA image, Haar features and/or RSID features can be calculated from an image patch centered at that voxel.

At step 208, each voxel in the CTA image is classified as bone or non-bone based on the landmark-based features and the image-based features using a trained voxel classifier. The voxel classifier is a machine learning based classifier trained based on image-based features and landmark-based features extracted from annotated training images. The trained voxel classifier can be a Random Forest classifier or a probabilistic boosting tree (PBT) classifier with boosted decision tree, but the present invention is not limited thereto. The trained voxel classifier calculates a probability for each voxel that the voxel is a bone structure based on the landmark-based features and the image-based features extracted for that voxel, and labels each voxel in the CTA image as bone or non-bone, resulting in a segmented bone mask for the CTA image. In an advantageous embodiment, intensity-based thresholding can be performed in the CTA image prior to applying the trained voxel classifier. This allows the trained voxel classifier to only consider sufficiently bright voxels whose intensities are above a certain intensity threshold. For example, all voxels>−224 Hounsfield Units (HU) may be considered to not accidently exclude marrow. In this case, the trained voxel classifier only evaluates the voxels whose intensity is greater than the intensity threshold and all remaining voxels are automatically considered to be non-bone.

The reliance on landmarks for landmark-based feature computations in the trained voxel classifier requires the use of one or more landmark detectors to detect the landmarks, as described above in connection with step 204. However, landmark detectors can and will fail for some cases, which will result in some missing landmarks, and therefore missing feature information. According to an advantageous embodiment, a Random Forest classifier can effectively deal with such missing feature information. Since a Random Forest classifier employs many decision trees, it is redundant, and some decision trees may not encounter missing feature information. Furthermore, decision trees in a Random Forest classifier can employ backup decision criteria. According to an advantageous embodiment, decision trees in the trained Random Forest Classifier can be implemented to determine backup splitting (classification) criteria in a customized way, as follows. The optimal decision criteria (i.e., features used to make the classification decision) is computed during training in the usual way, for example, by optimizing information gain using the $G_{ini}$ index. Other possible decision criteria are then ranked using a penalized measure of overlap and the top M criteria are selected as backup decision criteria The penalized measure of overlap can be defined as:

$$\text{PenalizedOverlap}(Y_{left}, Y_{right}) = |Y_{left} \cap Y_{left}^*| + |Y_{right} \cap Y_{right}^*| - \lambda |Y_{missing} \cap Y_{missing}^*|, \quad (1)$$

where $|\cdot|$ denotes the cardinality of a set, $Y_{left}$ and $Y_{right}$ denote the partitioning of training examples for some decision criteria and $Y_{left}^*$ and $Y_{right}^*$ denote the optimal partitioning of the training examples, $Y_{missing}$ and $Y_{missing}^*$ are the set of training examples where insufficient information is present to evaluate the corresponding decision criteria, and $\lambda$ is a tuning parameter that penalizes how similar the decision criteria are with respect to the missing information. In an exemplary implementation, $\lambda=2$, but the present invention is not limited thereto. This results in selecting decision criteria that not only has fewer missing examples, but also decision criteria that are missing on different example. When the trained Random Forrest voxel classifier to have back-up decision criteria that is different from the original decision criteria, the trained voxel classifier is more robust to missing landmark-based features due to a failed landmark detection.

Once the voxels in the CTA image are labeled as bone or non-bone, a regularization step may be applied to the resulting bone segmentation. In the regularization step, the CTA image is first segmented into supervoxels using a Watershed technique, and then each supervoxel is examined to see how many voxels in that supervoxel are labeled as bone. If more than a predetermined proportion of the supervoxel is labeled as bone, then the whole supervoxel is labeled as bone. Similarly, if more than a predetermined proportion of the supervoxel is labeled as non-bone, then the whole supervoxel is labeled as non-bone. The classification of the voxels in the CTA image as bone or non-bone can be used to generate a bone mask for the CTA image, which is a binary mask of the segmented bone voxels.

Figure 3:
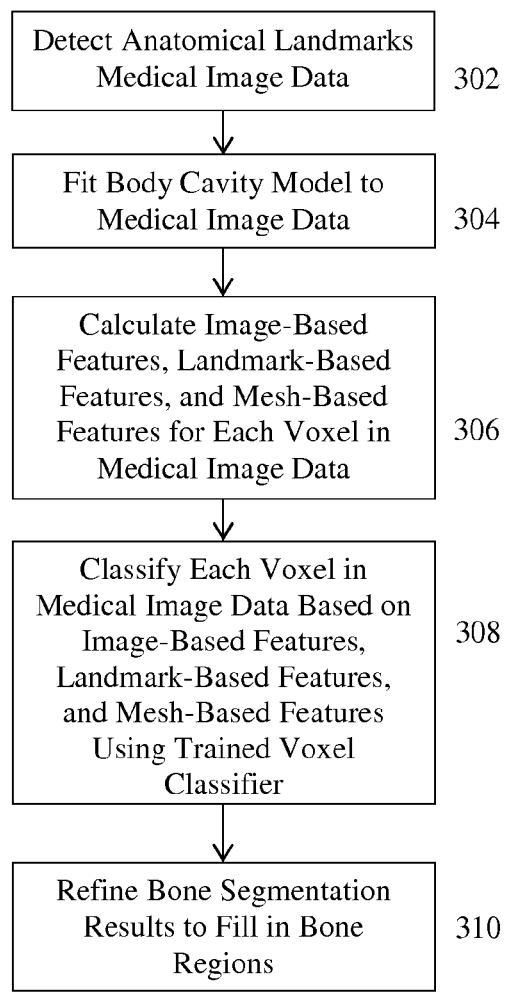
FIG. 3 illustrates a method for whole body bone segmentation in medical image data of a patient according to another embodiment of the present invention.

FIG. 3 illustrates a method for whole body bone segmentation in medical image data of a patient according to another embodiment of the present invention. The method of FIG. 3 can be used to implement step 104 of FIG. 1. The method of FIG. 3 can be used for non-contrast enhanced medical image data, such as a whole body CT volume, in addition to contrast enhanced medical image data, such as a CTA volume. Referring to FIG. 3, at step 302, a plurality of landmarks are detected in the medical image data. For examples, multiple bone and organ landmarks including, but not limited to vertebrae, sternum, ribs, femoral heads, hip bone corners, kidneys, liver, and lung may be detected in the medical image data. A trained landmark detector can be used to detect each of the plurality of landmarks. In an advantageous embodiment, a structured regression machine can be employed as the landmark detector to achieve fast landmark detection. The landmark detection may be implemented similarly to the landmark detection performed in step 202 of FIG. 2.

At step 304, a body cavity model is fit the medical image data based on the detected landmarks. A shape space of the body cavity can be learned from a set of training images and represented using principal component analysis (PCA). The PCA representation allows the a body cavity mesh to be fit to a 3D medical image based on a sparse and varying number of landmark points. Once the plurality of landmarks is detected in the medical image data of the patient, the learned PCA shape space of the body cavity is fit to at least a subset of the detected landmarks, resulting in a body cavity mesh. The region of the medical image data inside the body cavity mesh will generally have no bone. However, it is possible that the fitted mesh may have some inaccuracies that include some bone, so the body cavity mesh is not used as a hard constraint for the absence of bone. The body cavity mesh is used to compute features for machine learning based bone segmentation.

At step 306, image-based features, landmark-based features, and mesh-based features are calculated for each of the voxels in the medical image data. The image-based features can be Haar features and/or RSID features, and can be calculated for each voxel in an image patch centered at that voxel. The landmark-based features for a particular voxel in the medical image data can include the L1 and L2 distances between that voxel and each of the detected landmarks and axial projections of the offsets between that voxel each of the detected landmarks. The mesh-based features are calculated based on mesh points of the body cavity mesh. Mesh-based features for a particular voxel can be calculated using each mesh point of the body cavity mesh or a predetermined subset of the mesh points of the body cavity mesh. The mesh-based features for a particular voxel in the medical image data can include the L1 and L2 distances between that voxel and each of the mesh points and axial projections of the offsets between that voxel and each of the mesh points.

At step 308, the voxels in the medical image data are classified as bone or non-bone based on the image-based features, landmark-based features, and mesh-based features using a trained voxel classifier. The voxel classifier is a machine learning based classifier trained based on image-based features, landmark-based features, and mesh-based features extracted from annotated training images. The trained voxel classifier can be a Random Forest classifier or a probabilistic boosting tree (PBT) classifier with boosted decision tree, but the present invention is not limited thereto. The trained voxel classifier calculates a probability for each voxel that the voxel is a bone structure based on the landmark-based features, the image-based, and the mesh-based features extracted for that voxel, and labels each voxel as bone or non-bone, resulting in a segmented bone mask. In an advantageous implementation, the trained voxel classifier is a Random Forest classifier, and the Random Forest classifier is trained to select backup decision criteria using a penalized measure of overlap, as described above in connection with step 208 of FIG. 2

In an advantageous embodiment, intensity-based thresholding can be performed in the medical image data prior to applying the trained voxel classifier. This allows the trained voxel classifier to only consider sufficiently bright voxels whose intensities are above a certain intensity threshold. For example, all voxels>−224 Hounsfield Units (HU) may be considered to not accidently exclude marrow. In this case, the trained voxel classifier only evaluates the voxels whose intensity is greater than the intensity threshold and all remaining voxels are automatically considered to be non-bone.

Once the voxels in the CTA image are labeled as bone or non-bone, a regularization step may be applied to the resulting bone segmentation. In the regularization step, the CTA image is first segmented into supervoxels using a Watershed technique, and then each supervoxel is examined to see how many voxels in that supervoxel are labeled as bone. If more than a predetermined proportion of the supervoxel is labeled as bone, then the whole supervoxel is labeled as bone. Similarly, if more than a predetermined proportion of the supervoxel is labeled as non-bone, then the whole supervoxel is labeled as non-bone.

At step 310, the bone segmentation results are refined to fill holes in the bone structures. This step fills holes in the segmented structures corresponding to bone marrow voxels that were labeled as non-bone. First, a small closing operation is performed to close small openings to the tissue in the segmented bone structures, while not introducing too many artifacts from morphological operations. Then a region growing-based approach is used to fill small holes. The region-growing based approach can be implemented as follows: (1) Search for unlabeled (i.e., non-bone) voxels (label=0) that are neighbors of bone voxels (label=1). (2) For each such voxel, region grow up to N voxels (label=2). Here, N is the maximum size of the hole to consider. (3) If the hole size is <N, re-label the grown region as bone (label=1). In this algorithm, a label of 0 refers to unlabeled or non-bone voxels, a label of 1 refers to bone voxels, and a label of 2 refers to voxels included a grown region generated using region growing. This algorithm avoids redundantly growing on voxels that are shared by a surface, since those voxels would already be labeled as either 1 or 2.

Figure 4:
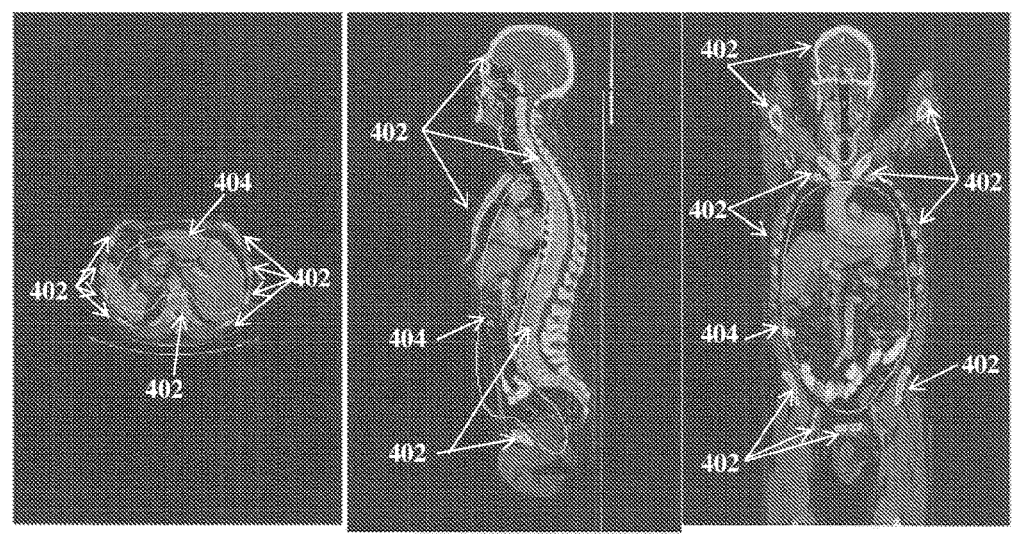
FIG. 4 illustrates exemplary results of whole body bone segmentation in a CT volume using the method of FIG. 3.

FIG. 4 illustrates exemplary results of whole body bone segmentation in a CT volume using the method of FIG. 3. In FIG. 4, segmented bone structures 402 are shown in three views of a CT volume. The body cavity mesh 404 is also shown in the three views of the CT volume.

Returning to FIG. 1, at step 106, vessel structures are segmented in the medical image data. The vessel segmentation in step 106 is performed independent of the bone segmentation in step 104, and results in a vessel mask for the medical image data. Bone segmentation itself does not guarantee the connectivity in the vessels, and there may sometimes be gaps or erosion in the vessels once bone removal is performed. Vessel segmentation in CTA images is challenging due to the varying appearance vessels and their proximity to bone. Vessels can also realize pathologies such as calcifications, stenoses, aneurysms, clots, and stents.

Figure 5:
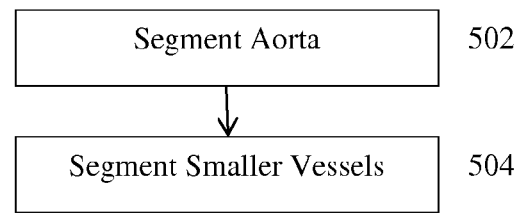
FIG. 5 illustrates a method for vessel segmentation in a medical image data of a patient image according to an embodiment of the present invention.

FIG. 5 illustrates a method for vessel segmentation in a medical image data of a patient image according to an embodiment of the present invention. The method of FIG. 5 can be used to implement step 106 of FIG. 1. In an advantageous embodiment, the method of FIG. 5 can be used to segment the vessels in a 3D CTA image of the patient, but the present invention is not limited thereto. Referring to FIG. 5, at step 502, the aorta is segmented in the medical image data. In a possible embodiment, intensity thresholding is first performed on the medical image data. This results in a binary mask including cortical bones and contrasted structures. The aorta and vertebrae tend to be loosely connected by only a few voxels. Next, a morphological erosion is performed to disconnect the aorta from the vertebrae, leaving the aorta as a single connected component. Then, each remaining connected component (after morphological erosion) is classified as aorta or not aorta. This can be performed by evaluating the voxels in each connected component with a trained classifier. The aorta connected components are then dilated back to their original size.

At step 504, smaller vessels are segmented in the medical image data. For example, once the aorta has been segmented, the remaining vessels can be segmented using a vessel tracing method or a sliced-based vessel segmentation method. In a possible implementation, larger arteries, such as the coronary arteries and the iliac artery can be segmented using a vessel tracing method and vertical blood vessels can be segmented using a slice-base method. Any known vessel tracing technique can be used to perform the vessel tracing segmentation.

Since vessels tend to be oriented vertically in the body, a sliced-based 2D connected component approach can be used to segment the vessels. For each horizontal slice (axial slice), intensity thresholding is first performed to produce a binary mask of bright structures in that slice. A 2D connected component analysis is then performed on the binary mask for the slice. In the 2D connected component analysis, small connected components that are sufficiently circular are labeled as vessels. It is determined if a connected component is sufficient circular by calculating a "circleness" measure, which computed the density of the connected component relative to a circle. The circleness measure can be expressed as:

$$\text{Circleness} = \frac{|X|}{(\pi * r^2)}, \quad (2)$$

where X is the set of all points in the connected component and r is the radius of the connected component defined as r=max(dist(p,c)), where p is a point in X and c is the centroid of X. In an exemplary implementation, a connected component is considered to be sufficiently circular if Circleness>0.8. This slice-based process results in segmentation of small vertical segments of vessels in each horizontal slice.

Figure 6:
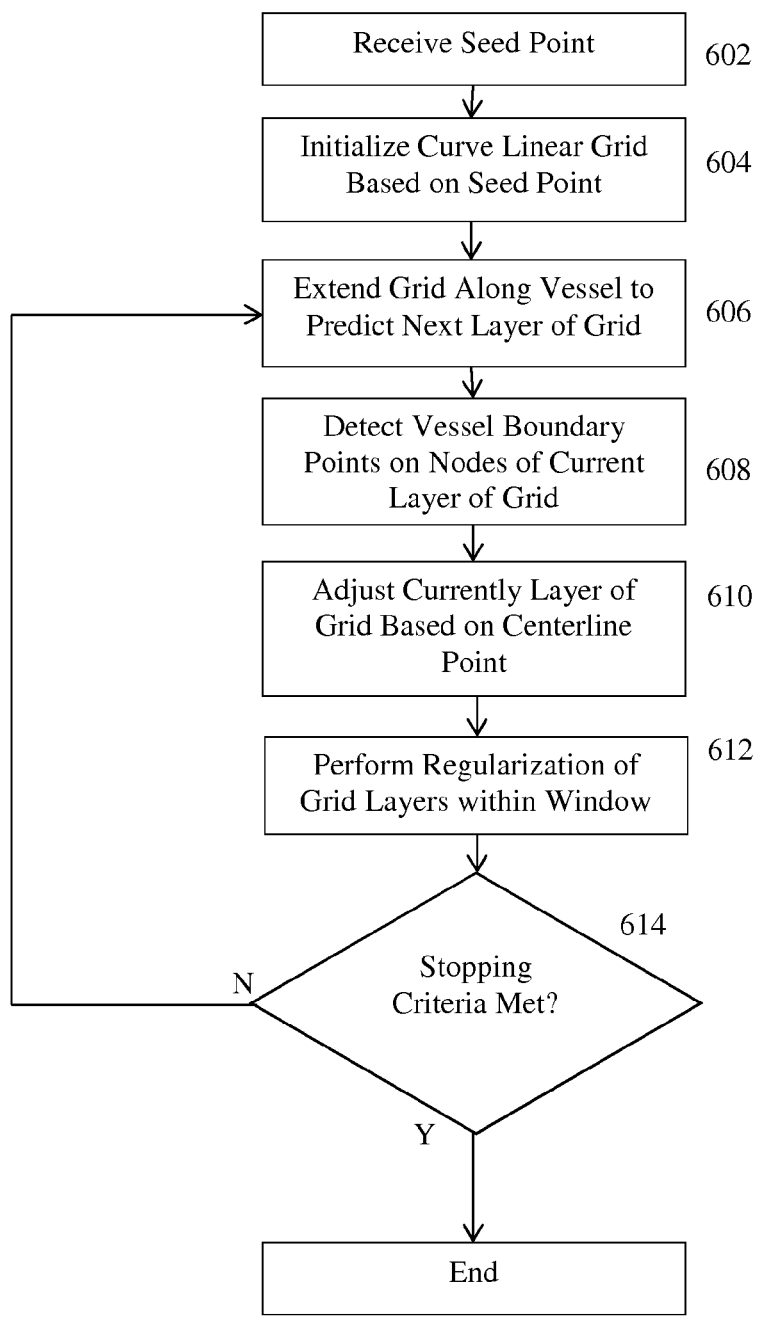
FIG. 6 illustrates a method of vessel segmentation in medical image data according to another embodiment of the present invention.

FIG. 6 illustrates a method of vessel segmentation in medical image data according to another embodiment of the present invention. The method of FIG. 6 can be used to implement step 106 of FIG. 1. The method of FIG. 6 can also be used to implement step 504 in FIG. 5. In a possible implementation, the method of FIG. 6 can be used to segment vessels in certain regions, such as the head and neck region, or in cases in which the method of FIG. 5 is not effective. The method of FIG. 6 is a tracking method that simultaneously optimizes the boundary and the centerline of a tubular structure representing the vessel. Referring to FIG. 6, at step 602, a seed point for a vessel is received. The seed point can be a starting point for tracking the vessel using the method of FIG. 6. In an advantageous embodiment, seed points for various vessels can be generated automatically in order to perform fully automatic segmentation of vessels in an image. For example, in a possible implementation a small set of voxels in a CTA image with intensity greater than a certain value can be randomly selected as seed points. The vessels are contrasted in the CTA image, hence they are bright. This may lead to some bone voxels being wrongly included as seeds, but these seeds can be removed by examining the voxel neighborhood and checking the shape. In another possible implementation, seed points can be automatically selected by performing intensity thresholding in axial (horizontal) slices, performing connected component analysis on bright voxels in the axial slices, selecting connected sufficiently circular connected components as seed points, as described above in connection with the method of FIG. 5. Alternatively, the seed point for a vessel can be received via a user input using a user input device, such as a mouse, touch screen, etc.

Figure 7:
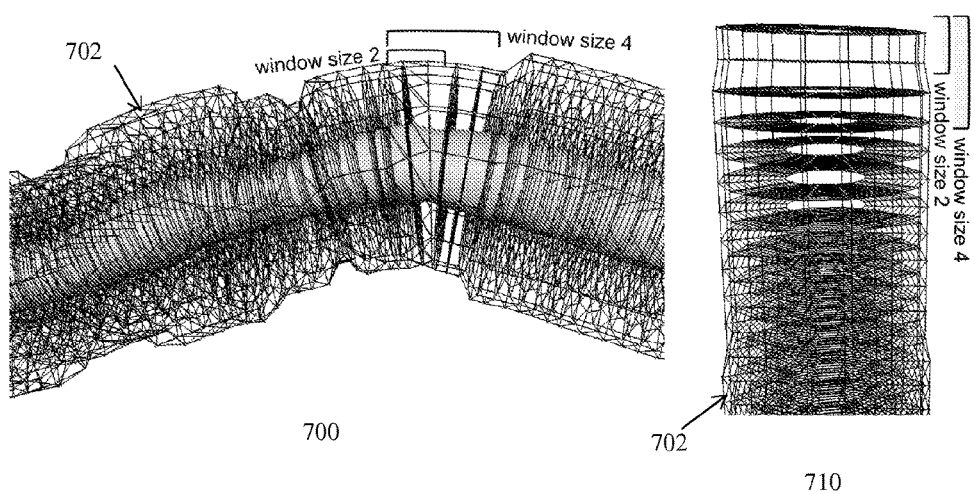
FIG. 7 illustrates segmentation of a vessel boundary using a curve linear grid.

At step 604, a curve linear grid is initialized based on the seed point. According to an advantageous implementation, a polar coordinate representation of an area surrounding a vessel centerline is used to discretize the tangent space of the tube representing the vessel. Connecting the polar coordinate points in a circular direction, radial direction, and a trajectory direction, creates a grid that can discretize the inside and the surrounding area of the approximately tubular vessel. This grid is referred to herein as a curve linear grid. FIG. 7 illustrates segmentation of a vessel boundary using a curve linear grid. As shown in FIG. 7, image 700 shows a curve linear grid 702 in world space and a resulting vessel boundary surface 704 segmented using the curve linear grid 702. Image 710 shows the curve linear grid 702 in tangent space. Each layer in the curve linear grid 702 is shaped like a circle or disk and corresponds to a particular cross-sectional slice of the vessel. The grid is constructed layer by layer on the fly, and each layer is used to estimate the center point and outer boundary of the vessel at that point in the trajectory direction. In order to initialize the curve linear grid based on the seed point, a trained machine learning based centerline classifier is used to evaluate an area surrounding the seed point to find the best centerline point near the seed point. An exhaustive search over different geometries and orientations can then be performed to find the orientation of the grid, trajectory direction, and boundary points for the vessel on the grid, that maximize a centerline probability of the centerline point calculated by the trained centerline classifier and a boundary probability of the boundary points calculated by a trained machine learning based boundary classifier.

At step 606, the curve linear grid is extended along the vessel (in the trajectory direction) to predict a next layer of the grid. The next grid layer is predicted based on the current grid geometry only. For example, the current grid geometry, including orientation, node locations and spacing, and trajectory direction can be moved a predetermined step size in the trajectory direction in the trajectory direction in order to predict the next layer in the grid. At this point, the method of FIG. 6 moves to the predicted next layer, such that the next layer predicted at this step will be referred to as the current layer.

At step 608, vessel boundary points are detected for the current layer of the grid based on the predicted grid geometry. In particular, the trained boundary classifier evaluates each node in the current layer of the grid to detect the grid nodes in the current layer that have the highest boundary classifier responses. This provides an initial estimate for the vessel boundary at the current point on the vessel, as well as an initial estimate of the tubular shape of the vessel at the current point.

At step 610, the current layer of the curve linear grid is adjusted based on a detected centerline point at the current location in the vessel. In particular, the trained centerline classifier can be used to detect a centerline point for the current layer of the grid by detecting a point with the highest centerline classifier response within the initial vessel boundary estimate for the current grid layer. The grid geometry (e.g., orientation, node locations/spacing) of the current layer of the grid is then adjusted to align the center of the grid with the detected centerline point while maintaining the initial tubular shape detected for the vessel boundary and maximizing the response of the boundary classifier at the detected boundary nodes of the current grid layer.

At step 612, regularization of grid layers within a certain window is performed. The regularization computes a smooth partitioning of the nodes of the grid into and inside set and an outside set, where the boundary between the inside set and the outside set represents the vessel surface. This can be performed using a graph-based segmentation algorithm such as graph cuts or random walks. This regularization can be performed for the current grid layer together with previously generated grid layers within a certain window. For example, if the window size is 1, only the last cross-section (layer) is optimized. If the window size is 2, the last two layers are optimized together leading to a smoother solution. Images 700 and 710 show exemplary window sizes of 2 and 4. It is also possible that all existing layers can be regularized each time a new layer is introduced, but this may lead to high computational costs. Because of the grid connectivity orthogonal to the trajectory and in the direction of the trajectory, the solution of the regularization can be forced to be globally and locally smooth along the tubular vessel structure. In a possible implementation, steps 608, 610, and 612 can be iterated for a particular grid layer until convergence or sufficient precision is obtained.

Figure 8:
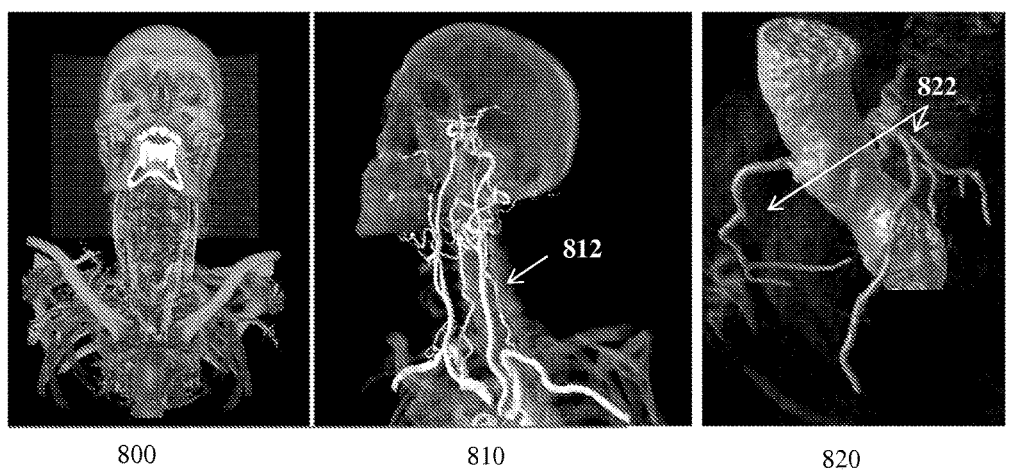
FIG. 8 illustrates exemplary vessel segmentation results using the method of FIG. 6.

At step 614, it is determined if a stopping criteria is met. For example, the stopping criteria may be, but is not limited to, length of the segmented vessel, average classifier response along the boundary, or touching of existing segmented structures. If it is determined that the stopping criteria is not yet met, the method returns to step 606 and extends the grid along the vessel to predict a next layer and then performs steps 608, 619, and 612 (possibly for multiple iterations) for the next layer. If it is determined that the stopping criteria is met, the method ends. FIG. 8 illustrates exemplary vessel segmentation results using the method of FIG. 6. As shown in FIG. 8, image 800 shows a noisy learning-based vessel classifier response in a head and neck region and image 810 shows a segmented vessel tree 812 in the head and neck region generated using the method of FIG. 6. In the segmented vessel tree 812, false positive responses of the vessel classifier in bone regions have been rejected by the tubular model regularization. Image 820 shows segmented coronary vessels 822 generated using the tubular tracing method of FIG. 6.

Figure 9:
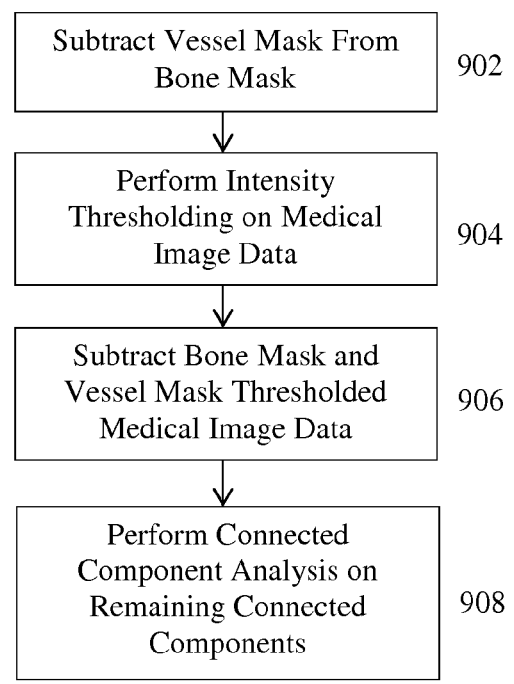
FIG. 9 illustrates a method for fusing bone segmentation results and vessel segmentation results according to an embodiment of the present invention.

Returning to FIG. 1, at step 108, the bone segmentation and the vessel segmentation are fused. Fusing the information from the independently performed bone and vessel segmentations increases the accuracy of the bone removal, as compared to using only the bone segmentation or the vessel segmentation to perform bone removal or vessel enhancement. This step refines the bone mask resulting from the bone segmentation and the vessel mask resulting from the vessel segmentation based on the fused information. FIG. 9 illustrates a method for fusing bone segmentation results and vessel segmentation results according to an embodiment of the present invention. The method of FIG. 9 can be used to implement step 108 of FIG. 1. At step 902, the vessel mask resulting from the vessel segmentation is subtracted from the bone mask resulting from the bone segmentation. The vessel mask is a binary mask that includes only those voxels labeled as vessels in the vessel segmentation. The bone mask is a binary mask including only those voxels labeled as bone in the bone segmentation. Subtracting the vessel mask from the bone mask has the effect of removing any voxels that were classified as both vessel and bone from the bone mask. Since the vessel segmentation may be more accurate than the bone segmentation, this step removes any vessel structure that was mistakenly classified as bone from the bone mask, and thus prevents mistakenly classified vessel voxels from being removed in the bone removal.

At step 904, intensity thresholding is performed on the medical image data. In particular, each voxel's intensity value can be compared to a predetermined threshold in order to generate a binary mask of bright structures in the medical image data. It is to be understood that such intensity thresholding may be performed once for the medical image data prior to the bone segmentation and the vessel segmentation, and the thresholded binary mask may be used in the bone segmentation and the vessel segmentation, as well as in the bone and vessel smoothing.

At step 906, the bone mask and the vessel mask are both subtracted from the thresholded medical image data. The bone mask and the vessel mask are both subtracted from the binary mask resulting from the intensity thresholding, such that only bright structures that have been labeled as neither bone nor vessel are remaining.

At step 908, connected component analysis is performed on the remaining connected components to assign labels to the remaining connected components. Once the remaining connected components that are labeled as neither bone nor vessel are identified in step 906, connected component analysis is performed on each such unlabeled connected component to assign a label to the unlabeled connected component based on neighboring labeled connected components in the binary mask resulting from the intensity thresholding. In an advantageous embodiment, the following rules can be used to assign a label to each unlabeled connected component: (1) If any neighboring connected component in the binary mask resulting from the intensity thresholding is labeled as a vessel, then label the unlabeled connected component as a vessel; (2) If the unlabeled connected component has no neighboring connected component labeled as a vessel, then label the unlabeled connected component as bone. Labeling connected components that share no bone or vessel neighbors as bone can have the effect of labeling equipment that is sometimes present in the scan as bone, and thus removing that equipment during the bone removal. This is beneficial, since the objective of the bone removal is to visualize the vessel tree.

Returning to FIG. 1, at step 110, bone removal is performed based on the fused bone segmentation and vessel segmentation results, and a visualization of the vessels in the medical image data is output. The bone removal is performed by subtracting the refined bone mask resulting from step 108 from the medical image data. This removes all segmented bone voxels from the medical image data, such that the only bright structures remaining are the vessels. In a possible implementation, the bone mask may be subtracted after intensity thresholding is performed. The resulting visualization of the vessels can be output, for example, by displaying the visualization of the vessels (i.e., the image with the bone voxels removed) on a display device of a computer system. In a possible implementation, the refined vessel mask resulting from step 108 can be used to provide vessel enhancement to the visualized vessels.

Figure 10:
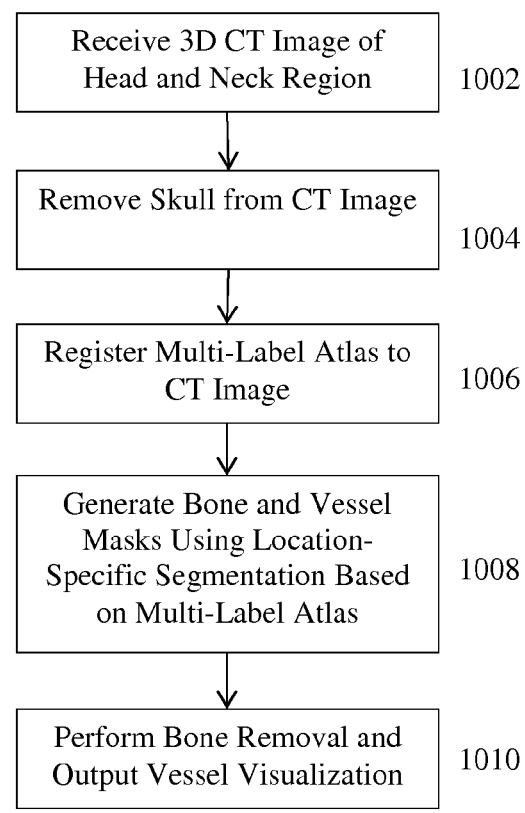
FIG. 10 illustrates a method for automatic bone removal in head and neck CT volumes according to an embodiment of the present invention.

As described above, the method of FIG. 1 can be used for whole body bone removal and vascular visualization. However, in another possible embodiment, a specialized bone removal method may be applied to images of a particular anatomical region, such as a head and neck region. FIG. 10 illustrates a method for automatic bone removal in head and neck CT volumes according to an embodiment of the present invention. The method of FIG. 10 transforms medical image data representing the anatomy of a patient to remove bone structures from the medical image data and generate a new medical image of the patient in which the bone structures have been removed and the vessel structures are enhanced. At step 1002, a 3D CT image of a head and neck region of a patient is received. The 3D CT image can be received directly from an image acquisition device, such as a CT scanner, or the 3D CT image can be received by loading a previously stored 3D CT image from a memory or storage of a computer system or receiving the 3D CT image in a network based transmission from another computer system. Although the method of FIG. 10 is described herein for a 3D CT image, the present invention is not limited thereto and other types of imaging modalities may be used as well.

At step 1004, the skull is removed from the 3D CT image. The skull voxels may be performed using standard skull removal techniques for medical image data. For example, a skull atlas can be registered with the 3D CT image and used to remove the skull voxels.

At step 1006, a multi-label atlas is registered to the 3D CT image. According to an advantageous embodiment, the multi-label atlas provides additional information in addition to the anatomy of the target image, and the additional information can be used to perform anatomy and location-specific segmentation of the bone and vessel structures in the 3D CT image. The multi-label atlas is generated offline prior to being registered to the target image by annotating the atlas with different labels. For example, in a possible implementation, soft tissue and air have the label 0, bones have the label 1, the main carotid artery has the label 2 below the skull base and the label 3 above the skull base, and the vertebralis artery has the label 4 when it is surrounded by bones and the label 5 when it is far from bones. In a possible implementation, multiple multi-label atlases can be used. The multi-label atlas(es) can provide information regarding anatomical variations such as relative distance of different bones from different vessels, thickness of different vessel lumens, intensity distribution of vessels, tissue, and bones, vessel pathologies such as stenosis and aneurysm, and other types of information. The multi-label atlas can be registered to the 3D CT image using standard atlas registration techniques.

At step 1008, bone and vessel masks are generated by performing anatomy and location-specific segmentation based on the registered multi-label atlas. For example, a graph-based segmentation method, such as graph cuts or random walker, can be used to perform segmentation of bone and vessel structures in each of the labeled regions in the 3D CT image corresponding to the registered multi-label atlas. According to an advantageous embodiment, a different set of parameters for the segmentation algorithm are associated with each label in the multi-label atlas, such that the segmentation algorithm (e.g., graph cuts or random walker) evaluates the voxels in the 3D CT image differently (i.e., using different parameters) based on the label assigned to voxels by the registered multi-label atlas.

Figure 11:
FIG. 11 illustrates anatomical differences between carotid and the vertebralis arteries.

FIG. 11 illustrates anatomical differences between carotid and the vertebralis arteries. As shown in FIG. 11, in a direction from toe to head, the carotid artery 1102 originates from the aorta and is located relatively far away from bones until is reaches the skull base. According to an advantageous embodiment, when the artery is far from bones (e.g., label 2), the segmentation parameters can be set such that nearby soft tissue voxels are preferred to be classified as vessel instead of bone. In terms of the final goal of rendering vessels and removing bones, this type of segmentation parameter is beneficial, as it lowers the risk of having missing vessel branches or having vessel gaps. In other words, "wrongly" classifying soft tissue adjacent to vessels as bones will not affect the final result for the carotid artery below the skull base (e.g., label 2). As shown in FIG. 11, the vertebralis arteries 1104, contrary to the carotid artery 1102, is tightly surrounded by bones at several places. When the artery is close to bones (e.g., label 4), the segmentation parameters can be set in a way that nearby soft tissue voxels are neutral to being classified as vessel or bone. In terms of the final goal of rendering vessels and removing bones, this type of segmentation parameter is beneficial, as it lowers the risk of falsely classifying bone as vessel, and vice versa. These two examples illustrate that that segmentation of the carotid and vertebralis arteries can be performed using different parameters. Such anatomy and location-specific segmentation parameters can be similarly applied to even finer anatomical granularity, such as categorizing the carotid artery into the main artery and the internal/external arteries, the area near the bifurcation (where the lumen in thicker). In this case each region of the carotid artery is labeled with a different label with the multi-label mask, and each region is segmented using different segmentation parameters.

In an advantageous implementation, the segmentation algorithm (e.g., graph cut or random walker) can use the following input information to perform the segmentation for each voxel in the 3D image: (1) The distance map of all nearby vessels within the registered multi-label atlas; (2) The distance map of all nearby bones within the multi-label atlas; and (3) The intensity constraints of vessel and bone (for example, contrasted vessels may have an intensity of within the range 100-1000 HU). For example, a function $F(D(x,y,z), \sigma)$ can be defined, where $\sigma$ is a some parameter, $(x,y,z)$ is a voxel, and $D(x,y,z)$ is the value of a distance map at $(x,y,z)$. In a possible implementation, the distance map can be the same size as the original volume, but in another possible implementation, the distance map can be the size of a region of interest. The function F is used in a graph cut segmentation algorithm and affects the final segmentation for the voxel $(x,y,z)$. The function F depends of the distance map D and one or more parameters represented as $\sigma$. According to an advantageous embodiment, the parameters $\sigma$ change bases on a label of the voxel $(x,y,z)$ and labels near the voxel $(x,y,z)$ in the registered multi-label atlas. For example, in an exemplary limitation, if $(x,y,z)$ is close to label A (e.g., the carotid artery), then the function F for that voxel can be defined as $F=F(D(x,y,z), \sigma=1)$. If the voxel $(x,y,z)$ is close to label B (e.g., a portion of the vertebralis artery surrounded by bone), the function F for that voxel can be defined as $F=F(D(x,y,z), \sigma=0.6)$.

Figure 12:
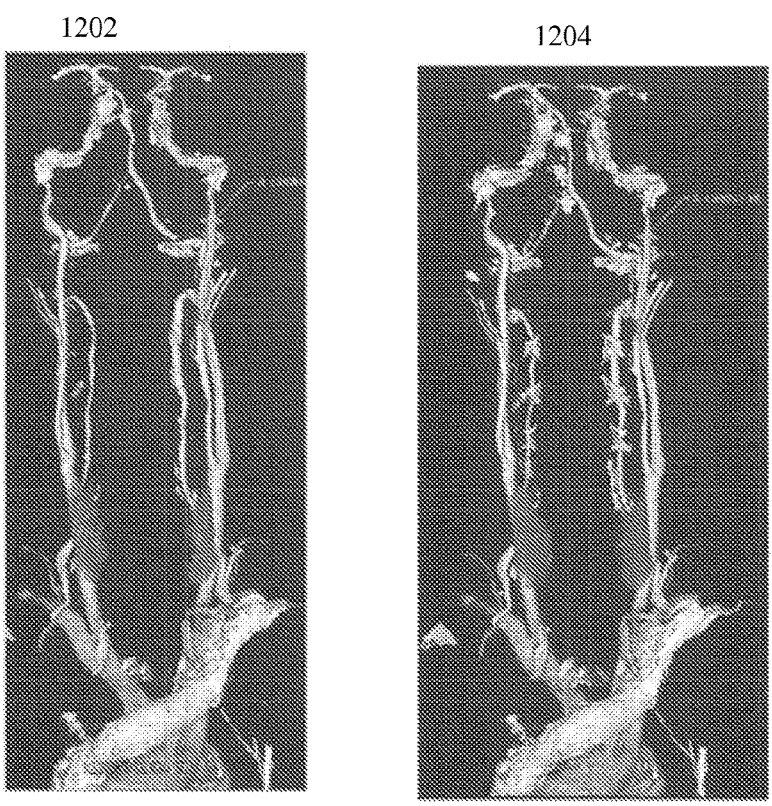
FIG. 12 illustrates exemplary bone removal results for a head and neck CT volume using the method of FIG. 10.

Returning to FIG. 10, at step 1010, bone removal is performed and a visualization of the vessels is output. The bone removal is performed by removing the voxels classified as bone and preserving and/or enhancing the voxels classified as vessel, resulting is a visualization of the vessels in the 3D CT image. The visualization of the vessels can be output, for example, by displaying the vessel visualization on a display device of a computer system. FIG. 12 illustrates exemplary bone removal results for a head and neck CT volume using the method of FIG. 10. Image 1202 of FIG. 12 shows a visualization of vessel structures in a hand and neck CT volume using the method of FIG. 10, which uses different segmentation parameters for different anatomies and locations. Image 1204 of FIG. 12 shows a visualization a vessel structures in the head and neck CT volume using a method that handles the segmentation of all vessels the same. As shown in FIG. 12, the visualization 1202 using the method of FIG. 10 yields cleaner segmentation results, as compared with the visualization 1204 in which many bone structures are attached to the final rendering of the vessels.

Figure 13:
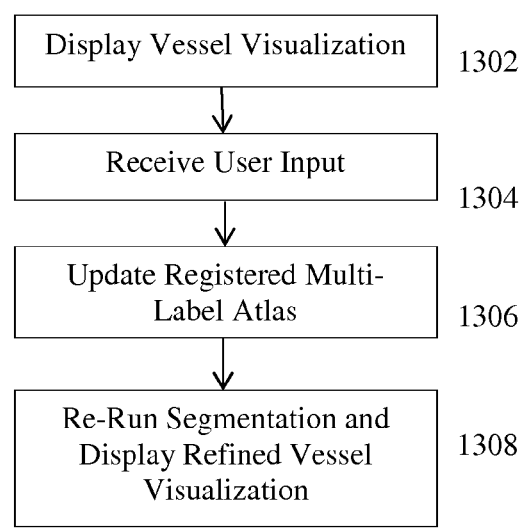
FIG. 13 illustrates a method for bone removal editing according to an embodiment of the present invention.

The above described methods of FIGS. 1 and 10 can be used to perform fully automatic bone removal and vessel visualization. However, it is possible that the vessel visualization resulting from such an automated bone removal method may still have bones occluding some vessel structures or may be missing portions of vessels that were mistakenly labeled as bone. Embodiments of the present invention provide editing systems and methods that allow users to manually edit the bones or vessels with a minimal user input (e.g., a minimum number of clicks). FIG. 13 illustrates a method for bone removal editing according to an embodiment of the present invention. The method of FIG. 13 provides a method for editing a vessel visualization resulting from the bone removal method of FIG. 10. The method of FIG. 13 transforms image data representing a vessel visualization resulting from a bone remove method and generates a refined vessel visualization. At step 1302, a vessel visualization is displayed. For example, a vessel visualization generated using the bone removal method of FIG. 10 can be displayed on a display device of a computer system.

At step 1304, user input is received. In particular, user input related to an incorrect portion of the displayed vessel visualization is received. The user input can be received via a user input device, such as a mouse or touchscreen. User inputs are referred to herein as "clicks", such as a mouse click, but it is to be understood that the user input is not limited to mouse clicks and any type of user input device may be used. Two embodiments are described herein for implementing the method of FIG. 13. The first embodiment if for "one-click" editing and the second embodiment is for "two-click" editing. These embodiments utilize the multi-label atlas that is registered to the medical image data and the anatomy and location-specific segmentation, as described in the method of FIG. 10. After the atlas registration, each voxel is assigned a label (e.g., from 0 to 5) according to the deformation field. In the one-click embodiment, the user provides a click point and a label (e.g., bone or vessel) associated with the click point. For example, the user may click on a bone structure that is occluding a portion of a vessel to label it as bone. In the two-click embodiment, the user places two clicks at the two ends of a straight vessel segment. For example, the user can click at opposite ends of a missing patch in a vessel that was mistakenly labeled as bone. Such a requirement is reasonable as a vessel can be approximated by multiple short vessel segments.

At step 1306, the registered multi-label atlas is updated based on the user input. For the one-click embodiment, the user clicks on a point associated with a label and the multi-label atlas stores the label for that point. In the two-click embodiment, the user places two clicks at opposite ends of a straight vessel segment. Given the two click points, linear interpolation is performed to estimate a straight line between the two click points, and all points along the line between the two click points are labeled as vessel and placed stored in the registered multi-label atlas.

At step 1308, the anatomy and location-specific segmentation is re-run using the updated registered multi-label atlas. In particular, a segmentation algorithm (e.g., graph cut or random walker) is performed on the medical image data with anatomy and location-specific parameters that vary based on the labels in the multi-label atlas to extract refined bone and vessel masks. According to an advantageous implementation, the segmentation algorithm (e.g., graph cut or random walker) uses the following information to perform the segmentation for each voxel: (1) The distance map of all nearby vessels within the registered multi-label atlas; (2) The distance map of all nearby bones within the multi-label atlas; (3) The intensity constraints of vessel and bone (for example, contrasted vessels may have an intensity of within the range 100-1000 HU); (4) The distance map of user click points that are labeled as vessel; and (5) The distance map of user click points that are labeled as bone. It is to be understood that the user click points in (4) and (5) include all of the points along the straight line estimated between the two user click points in the two-click embodiment. This segmentation results in refined bone and vessel masks which are used to perform bone removal, resulting in a refined vessel visualization. The refined vessel visualization is displayed to the user. In an exemplary implementation, the segmentation can be re-run and the refined vessel visualization displayed in real-time or near real-time in response to receiving the user input.

Figure 14:
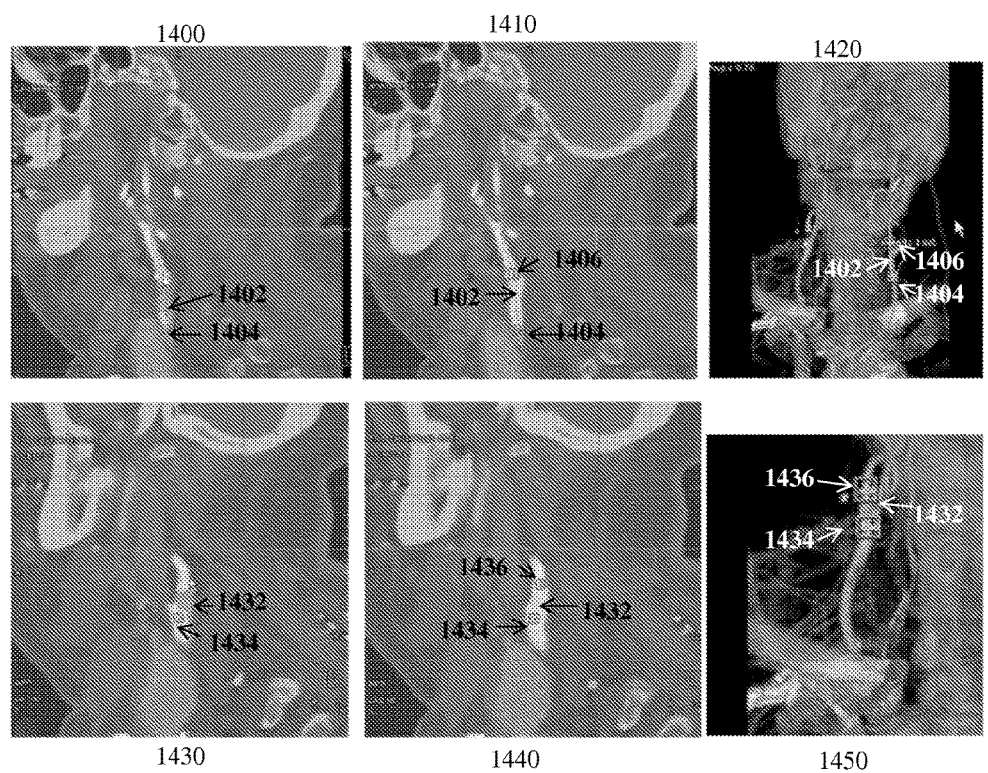
FIG. 14 illustrates exemplary results bone removal editing using the two-click embodiment.

FIG. 14 illustrates exemplary results of bone removal editing using the two-click embodiment. Images 1400, 1410, and 1420 of FIG. 14 show a first example of bone removal editing using the two-click embodiment. As shown in image 1400, there is a gap 1402 in a vessel in a displayed vessel visualization, and a first user click point 1404 is input at the lower part of the gap 1402. As shown in image 1410, a second user click point 1406 is received at the upper part of the gap 1402, and the gap 1402 is filled correctly using the method of FIG. 13. Image 1420 shows a 3D rendering of the refined vessel visualization in which the gap 1402 is filled in correctly. Images 1430, 1440, and 1450 of FIG. 14 show a second example of bone removal editing using the two-click embodiment. As shown in image 1430, there is a gap 1432 in a vessel in a displayed vessel visualization, and a first user click point 1434 is input at the lower part of the gap 1432. As shown in image 1440, a second user click point 1436 is received at the upper part of the gap 1432, and the gap 1432 is filled correctly using the method of FIG. 13. Image 1450 shows a 3D rendering of the refined vessel visualization in which the gap 1432 is filled in correctly.

One-click and two-click embodiments for the method of FIG. 13. In other possible implementations, the two-click embodiment can be extended to 3-click or 4-click (or more) embodiments, in which every click indicates a turning point of a vessel and the vessel centerline is interpolated or extrapolated using the click points.

Figure 15:
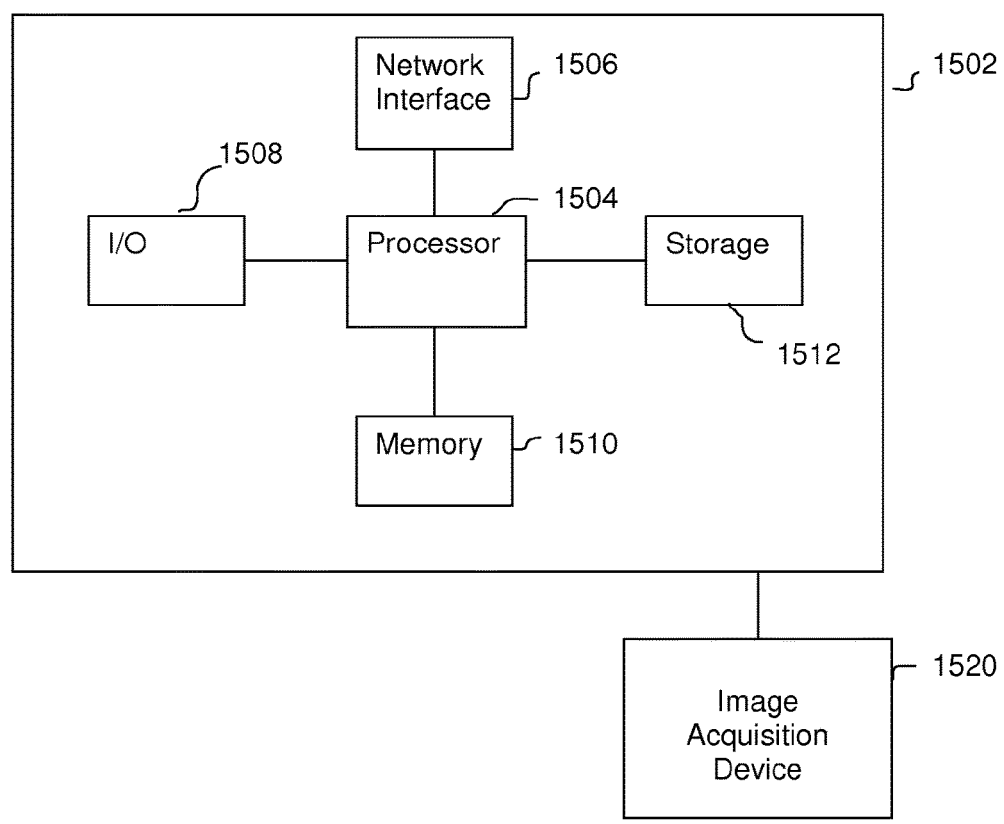
FIG. 15 is a high-level block diagram of a computer capable of implementing the present invention.

The above-described methods for bone removal, bone segmentation, vessel segmentation, and bone removal editing may be implemented on a computer using well-known computer processors, memory units, storage devices, computer software, and other components. A high-level block diagram of such a computer is illustrated in FIG. 15. Computer 1502 contains a processor 1504, which controls the overall operation of the computer 1502 by executing computer program instructions which define such operation. The computer program instructions may be stored in a storage device 1512 (e.g., magnetic disk) and loaded into memory 1510 when execution of the computer program instructions is desired. Thus, the steps of the methods of FIGS. 1, 2, 3, 5, 6, 9, 10, and 13 may be defined by the computer program instructions stored in the memory 1510 and/or storage 1512 and controlled by the processor 1504 executing the computer program instructions. An image acquisition device 1520, such as a CT scanning device, can be connected to the computer 1502 to input image data to the computer 1502. It is possible to implement the image acquisition device 1520 and the computer 1502 as one device. It is also possible that the image acquisition device 1520 and the computer 1502 communicate wirelessly through a network. In a possible embodiment, the computer 1502 can be located remotely with respect to the image acquisition device 1520 and the method steps described herein can be performed as part of a server or cloud based service. The computer 1502 also includes one or more network interfaces 1506 for communicating with other devices via a network. The computer 1502 also includes other input/output devices 1508 that enable user interaction with the computer 1502 (e.g., display, keyboard, mouse, speakers, buttons, etc.). Such input/output devices 1508 may be used in conjunction with a set of computer programs as an annotation tool to annotate volumes received from the image acquisition device 1520. One skilled in the art will recognize that an implementation of an actual computer could contain other components as well, and that FIG. 15 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The above-described methods for medical image synthesis may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1, 2, 3, 5, 6, 9, 10, and 13. Certain steps of the methods described herein, including one or more of the steps of FIGS. 1, 2, 3, 5, 6, 9, 10, and 13, may be performed by a server or by another processor in a network-based cloud-computing system. Certain steps of the methods described herein, including one or more of the steps of FIGS. 1, 2, 3, 5, 6, 9, 10, and 13, may be performed by a client computer in a network-based cloud computing system. The steps of the methods described herein, including one or more of the steps of FIGS. 1 and 2, may be performed by a server and/or by a client computer in a network-based cloud computing system, in any combination The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for bone removal and vessel visualization in a 3D medical image of a patient, comprising:
    segmenting bone structures in the 3D medical image, resulting in a bone mask of the 3D medical image;
    segmenting vessel structures in the 3D medical image, resulting in a vessel mask of the 3D medical image, wherein segmenting bone structures in the 3D medical image and segmenting vessel structures in the 3D medical image are performed independently with respect to each other;
    refining the bone mask and the vessel mask by fusing information from the bone mask and the vessel mask by:
        subtracting the vessel mask from the bone mask to remove any voxels segmented in the bone mask and the vessel mask from the bone mask,
        performing intensity-based thresholding on the 3D medical image to generate a binary thresholding mask of the 3D medical image,
        subtracting the bone mask and the vessel mask from the binary thresholding mask to identify unlabeled connected components of voxels in the thresholding mask, and
        labeling the unlabeled connected components of voxels in the thresholding mask based on labels of neighboring connected components in the thresholding mask; and
    removing bone voxels from the 3D medical image using the refined bone mask to generate a visualization of the vessel structures in the 3D medical image.

2. The method of claim 1, wherein removing bone voxels from the 3D medical image using the refined bone mask to generate a visualization of the vessel structures in the 3D medical image comprises:
    subtracting the refined bone mask from the 3D medical image.

3. The method of claim 1, further comprising:
    enhancing the vessel structures in the visualization of the vessel structures in the 3D medical image using the refined vessel mask.

4. The method of claim 1, wherein the 3D medical image is a 3D computed tomography angiography (CTA) image and removing bone voxels from the 3D medical image using the refined bone mask to generate a visualization of the vessel structures in the 3D medical image comprises:
    subtracting the refined bone mask from the binary thresholding mask resulting from performing intensity-based thresholding on the 3D CTA image.

5. The method of claim 1, wherein segmenting bone structures in the 3D medical image comprises:
    detecting a plurality of landmarks in the 3D medical image;
    calculating landmark-based features for each of a plurality of voxels in the 3D medical image based on the detected landmarks in the 3D medical image;
    calculating image-based features for each of the plurality of voxels in the 3D medical image;
    fitting a body cavity mesh having a plurality of mesh points to the 3D medical image;
    calculating mesh-based features for each of a plurality of voxels in the 3D medical image based on the mesh points of the body cavity mesh fitted to the 3D medical image; and
    classifying each of the plurality of voxels in the 3D medical image as bone or non-bone based on the landmark-based features, the image-based features, and the mesh-based features calculated for each of the plurality of voxels using a trained voxel classifier.

6. The method of claim 5, wherein segmenting bone structures in the 3D medical image further comprises:
    automatically refining the segmentation of the bone structures in the 3D image to fill in holes in the segmented bone structures.

7. The method of claim 6, wherein automatically refining the segmentation of the bone structures in the 3D image to fill in holes in the segmented bone structures comprises:
    identifying a voxel not labeled as bone that neighbors at least one voxel labeled as bone;

perform region growing up to N voxels for the identified voxel, where N is a predetermined maximum size hole to fill; and if a hole size for the identified voxel is less than N, label the grown region for the identified voxel as bone.

8. The method of claim 1, wherein segmenting vessel structures in the 3D medical image comprises:

segmenting an aorta in the 3D medical image using intensity-based thresholding and morphological operations; and segmenting remaining vessels in the 3D medical image at least one of vessel tracing or slice-based vessel segmentation.

9. The method of claim 8, wherein segmenting an aorta in the 3D medical image using intensity-based thresholding and morphological operations comprises:

performing intensity-based thresholding on the 3D medical image to generate a binary mask having connected components of bright voxels;

performing morphological erosion on the connected components to disconnect connected components representing the aorta from connected components representing vertebrae;

classifying each of the connected components resulting from the morphological erosion as aorta or non-aorta; and dilating the aorta connected components back to their original size.

10. The method of claim 8, wherein segmenting remaining vessels in the 3D medical image at least one of vessel tracing or slice-based vessel segmentation comprises:

detecting connected components of bright pixels in 2D horizontal slices of the 3D medical image; and labeling the connected components of bright pixels in the 2D horizontal slices as vessel or non-vessel based on a circleness measure of each connected component of bright pixels.

11. The method of claim 1, wherein segmenting vessel structures in the 3D medical image comprises, for at least one vessel in the 3D medical image:

estimating a centerline and boundary for the vessel in the 3D medical image by recursively generating a plurality of layers of a curve linear grid, wherein each layer of the curve linear grid corresponds to a cross-section of the vessel at a point along a length of the vessel and a centerline point and boundary points for the vessel are estimated at each layer of the curve linear grid.

12. The method of claim 11, wherein estimating a centerline and boundary for the vessel in the 3D medical image by recursively generating a plurality of layers of a curve linear grid, wherein each layer of the curve linear grid corresponds to a cross-section of the vessel at a point along a length of the vessel and a centerline point and boundary points for the vessel are estimated at each layer of the curve linear grid comprises:

for each layer of the curve linear grid:
predicting an initial grid geometry for a current layer of the curve linear grid based on the grid geometry for a previous layer of the curve linear grid;
detecting vessel boundary points on nodes of the current layer of the curve linear grid;
adjusting the grid geometry of the current layer of the curve linear grid based on a detected centerline point of the vessel; and regularizing the vessel boundary points for the current layer of the curve linear grid and a number of previous layers of the curve linear grid within a window.

13. The method of claim 12, wherein detecting vessel boundary points on nodes of the current layer of the curve linear grid comprises:

evaluating each of the nodes of the current layer of the curve linear grid using a trained boundary classifier to detect a number of nodes having highest boundary classifier responses.

14. The method of claim 12, wherein adjusting the grid geometry of the current layer of the curve linear grid based on a detected centerline point of the vessel comprises:

detecting the centerline point of the vessel within the detected vessel boundary points using a trained centerline classifier; and adjusting the grid geometry of the current layer of the curve linear grid to align a center of the current layer of the curve linear grid to the detected centerline point of the vessel.

15. The method of claim 12, wherein regularizing the vessel boundary points for the current layer of the curve linear grid and a number of previous layers of the curve linear grid within a window comprises:

performing graph-based segmentation on nodes of the current layer of the curve linear grid and the previous layers of the curve linear grid within the window to calculate a smooth partitioning of the curve linear grid within the window into a set of inside nodes and a set of outside nodes, wherein a boundary between the set of inside nodes and the set of outside nodes represents a surface of the vessel.

16. The method of claim 1, wherein labeling the unlabeled connected components of voxels in the thresholding mask based on labels of neighboring connected components in the thresholding mask comprises:

if any neighboring connected component to an unlabeled connected component in the thresholding mask is labeled as a vessel, labeling the unlabeled connected component as a vessel; and if an unlabeled connected component has no neighboring connected component in the thresholding mask that is labeled as a vessel, labeling the unlabeled connected component as a bone.

17. An apparatus for bone removal and vessel visualization in a 3D medical image of a patient, comprising:

means for segmenting bone structures in the 3D medical image, resulting in a bone mask of the 3D medical image;

means for segmenting vessel structures in the 3D medical image, resulting in a vessel mask of the 3D medical image, wherein segmenting bone structures in the 3D medical image and segmenting vessel structures in the 3D medical image are performed independently with respect to each other;

means for refining the bone mask and the vessel mask by fusing information from the bone mask and the vessel mask, comprising:

means for removing voxels segmented in the bone mask and the vessel mask from the bone mask, means for generating a binary thresholding mask of the 3D medical image, means for identifying unlabeled connected components of voxels in the thresholding mask, and means for labeling the unlabeled connected components of voxels in the thresholding mask based on labels of neighboring connected components in the thresholding mask; and means for removing bone voxels from the 3D medical image using the refined bone mask to generate a visualization of the vessel structures in the 3D medical image.

18. The apparatus of claim 17, wherein the means for segmenting vessel structures in the 3D medical image comprises:

means for segmenting an aorta in the 3D medical image using intensity-based thresholding and morphological operations; and means for segmenting remaining vessels in the 3D medical image at least one of vessel tracing or slice-based vessel segmentation.

19. The apparatus of claim 17, wherein the means for segmenting vessel structures in the 3D medical image comprises:

means for estimating a centerline and boundary for a vessel in the 3D medical image by recursively generating a plurality of layers of a curve linear grid, wherein each layer of the curve linear grid corresponds to a cross-section of the vessel at a point along a length of the vessel and a centerline point and boundary points for the vessel are estimated at each layer of the curve linear grid.

20. A non-transitory computer readable medium storing computer program instructions for bone removal and vessel visualization in a 3D medical image of a patient, the computer program instructions when executed by a processor cause the processor to perform operations comprising:

segmenting bone structures in the 3D medical image, resulting in a bone mask of the 3D medical image;

segmenting vessel structures in the 3D medical image, resulting in a vessel mask of the 3D medical image, wherein segmenting bone structures in the 3D medical image and segmenting vessel structures in the 3D medical image are performed independently with respect to each other;

refining the bone mask and the vessel mask by fusing information from the bone mask and the vessel mask by:

subtracting the vessel mask from the bone mask to remove any voxels segmented in the bone mask and the vessel mask from the bone mask, performing intensity-based thresholding on the 3D medical image to generate a binary thresholding mask of the 3D medical image, subtracting the bone mask and the vessel mask from the binary thresholding mask to identify unlabeled connected components of voxels in the thresholding mask, and labeling the unlabeled connected components of voxels in the thresholding mask based on labels of neighboring connected components in the thresholding mask; and removing bone voxels from the 3D medical image using the refined bone mask to generate a visualization of the vessel structures in the 3D medical image.

21. The non-transitory computer readable medium of claim 20, wherein segmenting vessel structures in the 3D medical image comprises:

segmenting an aorta in the 3D medical image using intensity-based thresholding and morphological operations; and segmenting remaining vessels in the 3D medical image at least one of vessel tracing or slice-based vessel segmentation.

22. The non-transitory computer readable medium of claim 20, wherein segmenting vessel structures in the 3D medical image comprises, for at least one vessel in the 3D medical image:

estimating a centerline and boundary for the vessel in the 3D medical image by recursively generating a plurality of layers of a curve linear grid, wherein each layer of the curve linear grid corresponds to a cross-section of the vessel at a point along a length of the vessel and a centerline point and boundary points for the vessel are estimated at each layer of the curve linear grid.

23. The non-transitory computer readable medium of claim 20, wherein labeling the unlabeled connected components of voxels in the thresholding mask based on labels of neighboring connected components in the thresholding mask comprises:

if any neighboring connected component to an unlabeled connected component in the thresholding mask is labeled as a vessel, labeling the unlabeled connected component as a vessel; and if an unlabeled connected component has no neighboring connected component in the thresholding mask that is labeled as a vessel, labeling the unlabeled connected component as a bone.

* * * * *